(12) United States Patent
Puentener et al.

(10) Patent No.: US 7,781,586 B2
(45) Date of Patent: Aug. 24, 2010

(54) METATHESIS CATALYSTS

(75) Inventors: Kurt Puentener, Basel (CH); Michelangelo Scalone, Baslerstrasse (CH)

(73) Assignee: Hoffman-La Roche Inc., Nutley, NJ (US)

( * ) Notice: Subject to any disclaimer, the term of this patent is extended or adjusted under 35 U.S.C. 154(b) by 684 days.

(21) Appl. No.: 11/820,602

(22) Filed: Jun. 19, 2007

(65) Prior Publication Data

US 2008/0021219 A1 Jan. 24, 2008

(30) Foreign Application Priority Data

Jun. 30, 2006 (EP) .................... 06116373

(51) Int. Cl.
*C07F 15/00* (2006.01)
*C07C 15/46* (2006.01)
(52) U.S. Cl. .................. 546/4; 556/137; 526/171; 585/438
(58) Field of Classification Search .......... 546/4; 556/137; 526/171; 585/438
See application file for complete search history.

(56) References Cited

FOREIGN PATENT DOCUMENTS

| EP | 1180108 | 8/2003 |
|---|---|---|
| WO | WO 02/14376 | 2/2002 |
| WO | WO 2004/035596 | 4/2004 |

OTHER PUBLICATIONS

Gstrein et al., Journal of Polymer Science:Part A: Polymer Chemistry, vol. 45, pp. 3496-3500 (2007).*
Barbasiewicz et al in *Organometallics*, published on Web Jun. 17, 2006.
J. Huang, E. Stevens, S. Nolan, J. Petersen, *J. Am. Chem. Soc.* 1999, 121, 2674-2678.
S. Varray, R. Lazaro., J. Matinez, F. Lamaty, *Organometallics* 2003, 22, 2426-2435.

* cited by examiner

*Primary Examiner*—Porfirio Nazario Gonzalez
(74) *Attorney, Agent, or Firm*—George W. Johnston; Patricia S. Rocha-Tramaloni

(57) ABSTRACT

Disclosed are novel metathesis catalysts of the formula

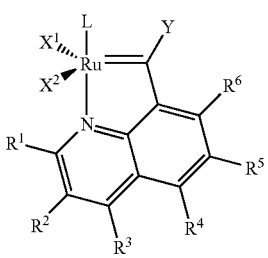

I wherein $R^1$, $R^2$, $R^3$, $R^4$, $R^5$, $R^6$, $X^1$, $X^2$, L and Y are as described herein, a process for making the same and their use in metathesis reactions such as ring closing or cross metathesis.

13 Claims, No Drawings

METATHESIS CATALYSTS

PRIORITY TO RELATED APPLICATION(S)

This application claims the benefit of European Patent Application No. 06116373.9, filed Jun. 30, 2006, which is hereby incorporated by reference in its entirety.

FIELD OF THE INVENTION

The invention relates to novel metathesis catalysts of the formula

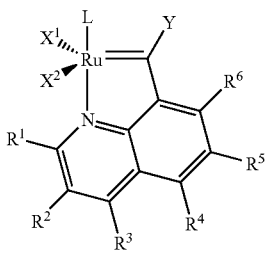

a process for making the same and their use in metathesis reactions such as ring closing or cross metathesis.

BACKGROUND OF THE INVENTION

Metathesis reactions using ruthenium or other transition metal complexes as catalysts are meanwhile well known and have been widely applied in organic synthesis (see e.g. WO 2004/035596, WO 2002/14376 or EP-A 1180108).

A metathesis catalyst of the formula

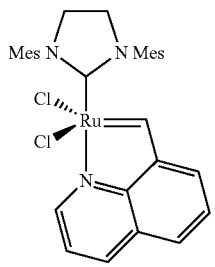

is described by Barbasiewicz et al in *Organometallics*, published on Web Jun. 17, 2006. The authors have shown that applying this catalyst in a ring closing metathesis reaction of N,N-diallyl-4-methylbenzenesulfonamide in dichloromethane at room temperature 41% of 1-(toluene-4-sulfonyl)-2,5-dihydro-1H-pyrrole was formed after a reaction time of 24 h. Upon reworking under the same conditions, the conversion was very poor (<3%) affording less than 1% of 1-(toluene-4-sulfonyl)-2,5-dihydro-1H-pyrrole and even at a higher reaction temperature (110° C. in toluene) the activity of this catalyst remained poor.

Object of the present invention therefore was to provide superior metathesis catalysts.

It was surprisingly found that a substitution in alpha position of the nitrogen atom significantly improved the activity of the catalysts.

It could be shown that the ruthenium complexes of formula I have the potential to be useful catalysts in metathesis reactions such as in the ring closing or cross metathesis reactions.

SUMMARY OF THE INVENTION

The present invention relates to compounds of the formula

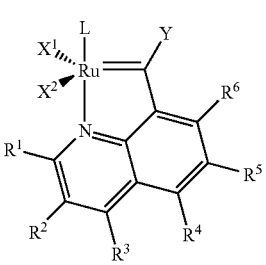

wherein $R^1$, $R^2$, $R^3$, $R^4$, $R^5$, $R^6$, $X^1$, $X^2$, L and Y are as described herein.

DETAILED DESCRIPTION OF THE INVENTION

The compounds of the present invention are characterized by the formula

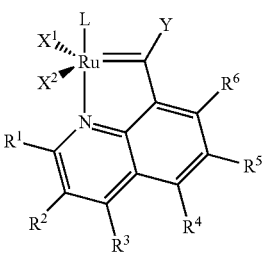

wherein

L is a neutral ligand;

$X^1$ and $X^2$ independently of each other are anionic ligands;

$R^1$ is selected from the group consisting of $C_{1-6}$-alkyl, halogen-$C_{1-6}$-alkyl, $C_{1-6}$-alkoxy, $C_{1-6}$-alkylcarbonyl, aryl, hydroxy, aryloxy, nitro, amino, mono-$C_{1-6}$-alkyl- or di-$C_{1-6}$-alkylamino, halogen, thio, $C_{1-6}$-alkylthio or $SO_2$—$C_{1-6}$-alkyl, $SO_2$-aryl, $SO_3H$, $SO_3$—$C_{1-6}$-alkyl or $OSi(C_{1-6}$-alkyl$)_3$ and $SO_2$—NR'R" wherein R' and R" independently of each other have the meaning of hydrogen or $C_{1-6}$-alkyl or R' and R" together with the N atom form a carbocycle;

$R^2$, $R^3$, $R^4$, $R^5$ and $R^6$ independently of each other are selected from the group consisting of hydrogen, $C_{1-6}$-alkyl, halogen-$C_{1-6}$-alkyl, $C_{1-6}$-alkoxy, $C_{1-6}$-alkylcarbonyl, aryl, hydroxy, aryloxy, nitro, amino, mono-$C_{1-6}$-alkyl- or di-$C_{1-6}$-alkylamino, halogen, thio, $C_{1-6}$-alkylthio or $SO_2$—$C_{1-6}$-alkyl, $SO_2$-aryl, $SO_3H$, $SO_3$—$C_{1-6}$-alkyl or $OSi(C_{1-6}$-alkyl$)_3$ and $SO_2$—NR'R" wherein R' and R" independently of each other have the meaning of hydrogen or $C_{1-6}$-alkyl or R' and R" together with the N atom form a carbocycle: and Y is selected from the group consisting of hydrogen, $C_{1-6}$-alkyl, $C_{2-6}$-alkenyl and aryl, or Y and $R^6$ taken together to form a (CH=CR)— or a —(CH$_2$)$_n$— bridge with n having the meaning of 2 or 3 and R as defined for R$^2$.

The present invention further includes a process for the preparation of the compounds of formula I and its use in metathesis reactions.

The following definitions are set forth to illustrate and define the meaning and scope of the various terms used to describe the invention herein.

The term "alkyl", alone or in combination with other groups, refers to a branched or straight-chain monovalent saturated aliphatic hydrocarbon radical of one to six carbon atoms, preferably one to four carbon atoms. This term is further exemplified by radicals as methyl, ethyl, n-propyl, isopropyl, n-butyl, s-butyl, t-butyl, 1-adamantyl and the groups specifically exemplified herein.

The term "alkenyl", alone or in combination with other groups, refers to a branched or straight-chain monovalent unsaturated aliphatic hydrocarbon radical of two to six carbon atoms, preferably two to four carbon atoms. This term is further exemplified by radicals as vinyl and propenyl, butenyl, pentenyl and hexenyl and their isomers. Preferred alkenyl radical is vinyl.

The term "halogen" refers to fluorine, chlorine, bromine and iodine. Preferred halogen is chlorine.

The term "halogen-C$_{1-6}$-alkyl" refers to a halogen substituted C$_{1-6}$-alkyl radical wherein halogen has the meaning as above. Preferred "halogen-C$_{1-6}$-alkyl" radicals are the fluorinated C$_{1-6}$-alkyl radicals such as CF$_3$, CH$_2$CF$_3$, CH(CF$_3$)$_2$, C$_4$F$_9$.

The term "alkoxy" refers to a branched or straight-chain monovalent saturated aliphatic hydrocarbon radical of one to six carbon atoms, preferably 1 to four carbon atoms attached to an oxygen atom. Examples of "alkoxy" are methoxy, ethoxy, propoxy, isopropoxy, butoxy, isobutoxy and hexyloxy. Preferred are the alkoxy groups specifically exemplified herein.

The alkyl chain of the alkoxy group can optionally be substituted, particularly mono-, di- or tri-substituted by alkoxy groups as defined above, preferably methoxy, or ethoxy or by aryl groups, preferably phenyl.

Preferred substituted alkoxy group is the benzyloxy group.

The term "alkyl carbonyl" refers to a C$_{1-6}$-alkycarbonyl group preferably to a C$_{1-4}$-alkycarbonyl group. It includes for example acetyl, propanoyl, butanoyl or pivaloyl. Preferred alkyl carbonyl group is acetyl.

The term "alkylthio" refers to the group R'—S—, wherein R' is C$_{1-6}$-alkyl, preferably C$_{1-4}$-alkyl e.g. methylthio or ethylthio. Preferred are the alkylthio groups specifically exemplified herein.

The term "SO$_2$—C$_{1-6}$-alkyl" refers to a sulfonyl substituted C$_{1-6}$-alkyl radical. Preferred SO$_2$—C$_{1-6}$-alkyl radical is SO$_2$-methyl.

The term "SO$_2$-aryl" refers to a sulfonyl substituted aryl radical. Preferred SO$_2$-aryl radical is SO$_2$-phenyl.

The term "SO$_2$—NR'R''" refers to a sulfonyl substituted amino group NR'R'' wherein R' and R'' independently of each other have the meaning of hydrogen or C$_{1-6}$-alkyl or R' and R'' together with the N atom form a carbocycle. Preferred SO$_2$—NR'R'' radicals is SO$_2$—N(methyl)$_2$.

The term "OSi(C$_{1-6}$-alkyl)$_3$" refers to a tri-C$_{1-6}$-alkyl-substituted silyloxy group. Preferred meaning of OSi(C$_{1-6}$-alkyl)$_3$ are trimethylsilyloxy, triethylsilyloxy and t-butyldimethylsilyloxy.

The term "mono- or di-alkyl-amino" refers to an amino group, which is mono- or disubstituted with C$_{1-6}$-alkyl, preferably C$_{1-4}$-alkyl. A mono-C$_{1-6}$-alkyl-amino group includes for example methylamino or ethylamino. The term "di-C$_{1-6}$-alkyl-amino" includes for example dimethylamino, diethylamino or ethylmethylamino. Preferred are the mono- or di-C$_{1-4}$-alkylamino groups specifically exemplified herein. It is hereby understood that the term "di-C$_{1-6}$-alkyl-amino" includes ring systems wherein the two alkyl groups together with the nitrogen atom to which they are attached form a 4 to 7 membered heterocycle which also may carry one further hetero atom selected from nitrogen, oxygen or sulfur.

The terms "amino" and "mono- or di-alkyl-amino" also encompass a group of the formula —NR'R''H$^+$Z$^-$ wherein R' and R'' are as above and Z$^-$ is an anion such as a halogenide, particularly chloride or a sulfonate, particularly methansulfonate or p-toluenesulfonate.

The term "cycloalkyl" denotes a "C$_{3-7}$-cycloalkyl" group containing from 3 to 7 carbon atoms, such as cyclopropyl, cyclobutyl, cyclopentyl, cyclohexyl or cycloheptyl.

The term "aryl" relates to the phenyl or naphthyl group, preferably the phenyl group, which can optionally be mono-, di-, tri- or multiply-substituted by halogen, hydroxy, CN, CF$_3$, NO$_2$, NH$_2$, N(H,alkyl), N(alkyl)$_2$, carboxy, aminocarbonyl, alkyl, alkoxy, alkylcarbonyl, SO$_2$-alkyl, SO$_2$-aryl, SO$_3$H, SO$_3$-alkyl, SO$_2$—NR'R'', aryl and/or aryloxy. Preferred aryl group is phenyl.

The term "aryloxy" relates to an aryl radical attached to an oxygen atom. The term "aryl" has the meaning as defined above. Preferred aryloxy group is phenyloxy.

The term "heteroaryl" relates to a heterocyclic aryl radical containing 1 to 3 heteroatoms in the ring with the remainder being carbon atoms. Suitable heteroatoms include, without limitation, oxygen, sulfur, and nitrogen. Exemplary heteroaryl groups include furanyl, thienyl, pyridyl, pyrrolyl, N-alkyl pyrrolo, pyrimidyl, pyrazinyl, imidazolyl, benzofuranyl, quinolinyl, and indolyl. Like the aryl group the heteroaryl group can optionally be mono-, di-, tri- or multiply-substituted by halogen, hydroxy, CN, CF$_3$, NO$_2$, NH$_2$, N(H, alkyl), N(alkyl)$_2$, carboxy, aminocarbonyl, alkyl, alkoxy, alkylcarbonyl, SO$_2$-alkyl, SO$_2$-aryl, SO$_3$H, SO$_3$-alkyl, SO$_2$—NR'R'', aryl and/or aryloxy.

The ligand L is a neutral ligand preferably selected from the group consisting of —P(R$^{10}$)$_3$:

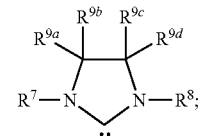

IIa

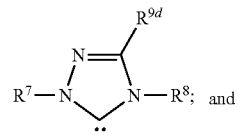

IIb; and

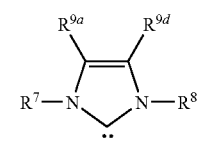

IIc wherein

R[7] and R[8] independently of each other are $C_{1-6}$-alkyl, aryl, $C_{2-6}$-alkenyl or 1-adamantyl and R[9a-d] are independently of each other hydrogen, $C_{1-6}$-alkyl, $C_{2-6}$-alkenyl or aryl, or R[9b] and R[9c] or R[9a] and R[9d] taken together form a —(CH$_2$)$_4$-bridge;

R[10] is independently of each other $C_{1-6}$-alkyl, $C_{3-7}$-cycloalkyl, aryl or heteroaryl In a preferred embodiment R[7] and R[8] are $C_{1-6}$-alkyl or a phenyl group which is di- or tri-substituted with $C_{1-6}$-alkyl. R[7] and R[8] more preferably are selected from t-butyl, 1-adamantyl, isopropyl, 2,6-diisopropylphenyl or 2,4,6-trimethylphenyl most preferably 2,4,6-trimethylphenyl.

In a preferred embodiment R[9a] and R[9c] are methyl or phenyl and R[9b] and R[9d] are hydrogen, or R[9a] and R[9c] or R[9b] and R[9d] are taken together to form a —(CH$_2$)$_n$— bridge with n having the meaning of 5 or 6. It is hereby understood that if chiral carbon atoms are present, both the racemic and the enantiomerically pure form are comprised.

In a further preferred embodiment R[9a-d] is hydrogen.

In a further preferred embodiment L is

IId

IIe wherein R[7] and R[8] are as described above.

In a further preferred embodiment R[10] is cyclohexyl.

As anionic ligand X[1] and X[2] a halogenide or a pseudo halogenide such as cyanide, a rhodanide, a cyanate, an isocycanate, acetate or trifluoroacetate may be selected. Preferred anionic ligand for X[1] and X[2] is a halogenide, whereas chloro is the most preferred anionic ligand.

In a further preferred embodiment R[1] is $C_{1-6}$-alkyl, halogen-$C_{1-6}$-alkyl or aryl. R[1] more preferably is methyl, trifluoromethyl, phenyl, ortho-tolyl or 2,6-dimethylphenyl.

In a further preferred embodiment R[2], R[4], R[5] and R[6] are hydrogen.

R[3] preferably is hydrogen, hydroxy, $C_{1-6}$-alkoxy, $C_{1-6}$-alkoxycarbonyl, nitro, amino or halogen.

More preferred R[3] stands for chloro, hydroxy, benzyloxy, amino, nitro or acetyl.

The following compounds represent the most preferred representatives of the present invention.

Abbreviations: ImH$_2$Mes=1,3-bis-(2,4,6-trimethylphenyl)-2-imidazolidinylidene; ImMes=1,3-bis-(2,4,6-trimethylphenyl)-2-imidazoylidene

| Table of catalysts tested: | |
|---|---|
| Catalyst Structure | Chemical Name |
| | [RuCl$_2$(ImH$_2$Mes)(8-quinolinylmethylene)] (Comparison example) |
| | [RuCl$_2$(ImH$_2$Mes)((4-chloro-2-trifluoromethyl-8-quinolinyl)methylene)] |
| | [RuCl$_2$(ImH$_2$Mes)((4-hydroxy-2-phenyl-8-quinolinyl)methylene)] |
| | [RuCl$_2$(ImH$_2$Mes)((4-chloro-8-quinolinyl)methylene)] (Comparison example) |
| | [RuCl$_2$(ImH$_2$Mes)((2-methyl-8-quinolinyl)methylene)] |

Table of catalysts tested:

| Catalyst Structure | Chemical Name |
|---|---|
| 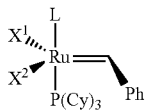 | [RuCl₂(tricyclohexylphosphine)((4-chloro-2-trifluoromethyl-8-quinolinyl)methylene)] |
| 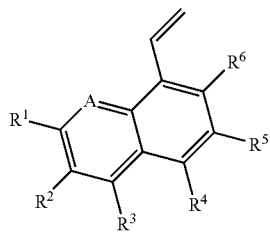 | [RuCl₂(ImMes)((4-chloro-2-trifluoromethyl-8-quinolinyl)methylene)] |

The present invention also comprises a process for the preparation of a compound of the formula I which comprises the transformation of a Ru-precursor compound of the formula III

III wherein $X^1$ and $X^2$ are as defined, Cy has the meaning of cyclohexyl and Ph is phenyl with a compound of formula IV

IV wherein $R^1$ to $R^6$ have the meaning as above.

The conversion as a rule takes place in an organic solvent like toluene, benzene, tetrahydrofuran or dichloromethane in the presence of a copper salt, preferably copper chloride at a temperature of about 0° C. to 60° C.

The compounds of formula IV can be prepared by several well known cross-coupling reactions which are e.g. described in F. Diederich and P. J. Stang in 'Metal-catalyzed cross-coupling reactions' Wiley-VCH, 1998 or J. March in 'Advanced organic chemistry' Wiley-VCH, 1992 starting from commercially available or easy accessible compounds of formula V with e.g. vinylstannanes, ethylene, vinylboronates, vinylboranes, vinyl Grignard reagents or under Wittig, Wittig-Horner, Wittig-Horner-Emmons, Tebbe or Peterson conditions starting from commercially available aldehydes of formula VI.

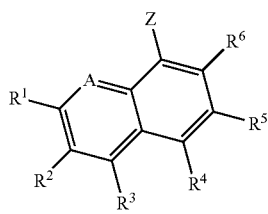

V

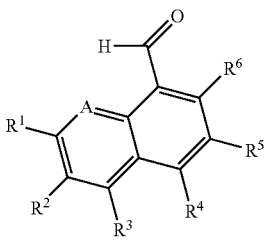

VI wherein Z is halogen or trifluoromethansulfonyloxy and $R^1$ to $R^6$ have the meaning as above.

The compounds of the present invention can be used in metathesis reactions particularly in ring closing or cross metathesis reactions. Though it is apparent for the skilled in the art that reaction conditions have to be adapted for each substrate, the following conditions can as a rule be applied.

Ring closing and cross metathesis reactions are usually performed in an inert organic solvent such as in toluene, xylene, mesitylene, and dichloromethane and at reaction temperatures from 20° C. to 180° C. Catalyst concentration is commonly selected between 0.1 mol % and 10 mol %.

The following examples illustrate the invention without limiting it.

EXAMPLES

Abbreviations: ImH₂Mes=1,3-bis-(2,4,6-trimethylphenyl)-2-imidazolidinylidene; ImMes=1,3-bis-(2,4,6-trimethylphenyl)-2-imidazolylidene

Table of Catalysts tested:

| Catalyst Structure | Chemical Name |
|---|---|
| | [RuCl₂(ImH2Mes)(8-quinolinylmethylene)] (Comparison example) |

Table of Catalysts tested:

| Catalyst Structure | Chemical Name |
|---|---|
| (structure) | [RuCl₂(ImH2Mes)((4-chloro-2-trifluoromethyl-8-quinolinyl)methylene)] |
| (structure) | [RuCl₂(ImH2Mes)((4-hydroxy-2-phenyl-8-quinolinyl)methylene)] |
| (structure) | [RuCl₂(ImH₂Mes)((4-chloro-8-quinolinyl)methylene)] (Comparison example) |
| (structure) | [RuCl₂(ImH₂Mes)((2-methyl-8-quinolinyl)methylene)] |
| (structure) | [RuCl₂(tricyclohexylphosphine)((4-chloro-2-trifluoromethyl-8-quinolinyl)methylene)] |
| (structure) | [RuCl₂(ImH2Mes)((4-chloro-2-trifluoromethyl-8-quinolinyl)methylene)] |

Synthesis of Catalysts

Examples 1-11

Example 1

[RuCl₂(ImH₂Mes) (8-quinolinylmethylene)]

A suspension of 500 mg (0.59 mmol) of [RuCl₂(PCy₃)(ImH₂Mes)(phenylmethy-lene)] (commercially available from Sigma-Aldrich Inc., St. Louis, USA), 60 mg (0.61 mmol) copper chloride and 100 mg (0.64 mmol) 8-vinylquinoline (prepared according to G. T. Crisp, S. Papadopoulos, *Aust. J. Chem.* 1989, 42, 279-285) in 40 ml methylene chloride was stirred at room temperature for 90 min. The reaction mixture was evaporated to dryness and the isolated crude product purified by silica gel chromatography (hexane/ethyl acetat 2:1) to yield 255 mg (70%) of the title compound as green crystals. MS: 584.4 (M-Cl⁺). ¹H-NMR (300 MHz, CD₂Cl₂): 2.36 (s, 6H); 2.40 (s, 12H); 4.04 (s, 4H); 7.01 (s, 4H); 7.19 (dd, J=8.4, 4.9 Hz, 1H); 7.34 (t, J=7.7 Hz, 1H); 7.51 (d, J=7.1 Hz, 1H); 8.08-8.18 (m, 2H); 8.26 (dd, J=4.8, 1.3 Hz, 1H); 16.95 (s, 1H). Anal. calcd. for $C_{31}H_{33}N_3Cl_2Ru$: C, 60.09; H, 5.37; N, 6.78; Cl, 11.44. Found: C, 60.06; H, 5.75; N, 6.16; Cl, 10.90.

Example 2

4-Chloro-2-trifluoromethyl-8-vinyl-quinoline

A suspension of 2.00 g (6.25 mmol) 8-bromo-4-chloro-2-trifluoromethylquinoline (commercially available from Maybridge, Cornwall, UK), 258 mg (0.31 mmol) PdCl₂dppf CH₂Cl₂, 1.29 g (9.37 mmol) potassium vinyl tetrafluoroborate and 0.88 ml (6.28 mmol) triethylamine in 40 ml ethanol was heated at reflux for 3 h. The resulting yellow suspension was filtered and the filtrate evaporated to dryness. The residue was suspended in ethyl acetate, filtered and the filtrate extracted with water. The organic layer was evaporated to dryness and the isolated crude product purified by silica gel chromatography (hexane) to yield 1.17 g (72%) of the title compound as white crystals. MS: 257.1 (M⁺). ¹H-NMR (300 MHz, CDCl₃): 5.58 (dd, J=11.1, 1.1 Hz, 1H); 6.07 (dd, J=17.8, 1.1 Hz, 1H); 7.75 (t, J=7.7 Hz, 1H); 7.81 (s, 1H); 7.99 (dd, J=17.8, 1.1 Hz, 1H); 8.09 (d, J=7.2 Hz, 1H); 8.23 (d, J=8.4 Hz, 1H).

Example 3

[RuCl$_2$(ImH$_2$Mes)((4-chloro-2-trifluoromethyl-8-quinolinyl)methylene)]

A suspension of 1.39 g (1.64 mmol) of [RuCl$_2$(PCy$_3$)(ImH$_2$Mes)(phenylmethy-lene)], 0.17 g (1.80 mmol) copper chloride and 464 mg (1.69 mmol) 4-chloro-2-trifluoromethyl-8-vinyl-quinoline in 100 ml methylene chloride was stirred at 30° C. for 90 min. The reaction mixture was evaporated to dryness and the isolated crude product purified by silica gel chromatography (hexane/ethyl acetate 5:2) to yield 278 mg (24%) of the title compound as green crystals. MS: 721.2 (M$^+$). $^1$H-NMR (300 MHz, CD$_2$Cl$_2$): 2.85 (s, 6H); 2.40 (s, 12H); 4.05 (s, 4H); 7.01 (s, 4H); 7.54 (s, 1H); 7.56 (t, J=7.7 Hz, 1H); 7.65 (d, J=6.8 Hz, 1H); 8.51 (d, J=8.4 Hz, 1H); 16.70-17.10 (br, 1H).

Example 4

2-Phenyl-8-vinyl-quinoline-4-ol

A suspension of 500 mg (1.67 mmol) 8-bromo-2-phenyl-quinoline-4-ol (commercially available from Ubichem Research Ltd, Budapest, Hungary), 97 mg (0.09 mmol) Pd(PPh$_3$)$_4$, 71 mg (1.67 mmol) lithium chloride and 528 mg (1.67 mmol) tributylvinyl stannane in 20 ml dioxane was heated at 90° C. for 16 h. The resulting yellow suspension was filtered and the filtrate evaporated to dryness. The residue was suspended in ethyl acetate, filtered and the filtrate extracted with water. The organic layer was evaporated to dryness and the isolated crude product purified by silica gel chromatography (ethyl acetate) to yield 178 mg (43%) of the title compound as yellowish crystals. $^1$H-NMR (300 MHz, CDCl$_3$): 5.59 (d, J=11.1 Hz, 1H); 5.75 (d, J=17.4 Hz, 1H); 6.42 (s, 1H); 7.04 (dd, J=17.4, 11.1 Hz, 1H); 7.23 (t, J=8.1 Hz, 1H); 7.40-7.60 (m, 6H); 8.21 (d, J=8.1 Hz, 1H); 8.70 (br, 1H).

Example 5

[RuCl$_2$(ImH$_2$Mes)((4-hydroxy-2-phenyl-8-quinolinyl)methylene)]

A suspension of 100 mg (0.12 mmol) of [RuCl$_2$(PCy$_3$)(ImH$_2$Mes)(phenylmethy-lene)], 12 mg (0.12 mmol) copper chloride and 100 mg (0.12 mmol) 2-phenyl-8-vinyl-quinoline-4-ol in 11 ml methylene chloride was stirred at 40° C. for 1 h. The reaction mixture was evaporated to dryness and the isolated crude product purified by silica gel chromatography (hexane/ethyl acetat 2:1) to yield 51 mg (61%) of the title compound as green crystals. MS: 711.1 (M$^+$). $^1$H-NMR (300 MHz, CD$_2$Cl$_2$): 2.32 (s, 12H); 2.41 (s, 6H); 3.90 (s, 4H); 6.12-6.28 (br, 1H); 6.80-6.92 (m, 2H); 6.98 (s, 4H); 7.04-7.14 (m, 1H); 7.19 (t, J=7.1 Hz, 1H); 7.29 (d, J=6.9 Hz, 1H); 7.35 (d, J=7.5 Hz, 2H); 7.49 (d, J=7.1 Hz, 1H); 7.80-8.00 (br, 1H); 17.34 (s, 1H).

Example 6

4-Chloro-8-vinyl-quinoline

A suspension of 975 mg (4.02 mmol) 8-bromo-4-chloro-quinoline (commercially available from Ubichem Research Ltd, Budapest, Hungary), 166 mg (0.20 mmol) PdCl$_2$dppfCH$_2$Cl$_2$, 833 mg (6.00 mmol) potassium vinyl tetrafluoroborate and 0.57 ml (4.10 mmol) triethylamine in 20 ml ethanol was heated at reflux for 3 h. The resulting yellow suspension was filtered and the filtrate evaporated to dryness. The residue was suspended in ethyl acetate, filtered and the filtrate extracted with water. The organic layer was evaporated to dryness and the isolated crude product purified by silica gel chromatography (hexane/ethyl acetate 9:1) to yield 207 mg (27%) of the title compound as white crystals. MS: 189.1 (M$^+$). $^1$H-NMR (300 MHz, CDCl$_3$): 5.53 (d, J=11.1 Hz, 1H); 5.95 (d, J=17.7 Hz, 1H); 7.51 (d, J=4.6 Hz, 1H); 7.63 (t, J=7.9 Hz, 1H); 7.96 (dd, J=17.7, 11.1 Hz, 1H); 7.97 (d, J=7.1 Hz, 1H); 8.19 (d, J=8.5 Hz, 1H); 8.80 (d, J=4.6 Hz, 1H).

Example 7

For Comparison

[RuCl$_2$(ImH$_2$Mes)((4-chloro-8-quinolinyl)methylene)]

A suspension of 790 mg (0.93 mmol) of [RuCl$_2$(PCy$_3$)(ImH$_2$Mes)(phenylmethy-lene)], 95 mg (0.96 mmol) copper chloride and 196 mg (1.03 mmol) 4-chloro-8-vinyl-quinoline in 70 ml methylene chloride was stirred at 30° C. for 90 min. The reaction mixture was evaporated to dryness and the isolated crude product purified by silica gel chromatography (hexane/ethyl acetat 5:2) and finally digested in 20 ml pentane at room temperature for 30 min to yield 311 mg (51%) of the title compound as green crystals. MS: 655.0 (M$^+$). $^1$H-NMR (300 MHz, CD$_2$Cl$_2$): 2.35 (s, 6H); 2.39 (s, 12H); 4.04 (s, 4H); 7.00 (s, 4H); 7.25 (d, J=5.3 Hz, 1H); 7.43 (dd, J=8.2, 7.3 Hz, 1H); 7.56 (dd, J=7.1, 0.7 Hz, 1H); 8.13 (d, J=5.3 Hz, 1H); 8.41 (dd, J=8.2, 0.7 Hz, 1H); 16.95 (s, 1H). Anal. calcd. for C$_{31}$H$_{32}$N$_3$Cl$_3$Ru: C, 56.93; H, 4.93; N, 6.42; Cl, 16.26. Found: C, 56.59; H, 5.04; N, 6.02; Cl, 15.49.

Example 8

2-Methyl-8-vinyl-quinoline

A suspension of 4.80 g (21.60 mmol) 8-bromo-2-methylquinoline (commercially available from ACB Block Ltd, Moscow, Russia), 0.89 g (1.10 mmol) PdCl$_2$dppfCH$_2$Cl$_2$, 4.48 g (32.40 mmol) potassium vinyl tetrafluoroborate and 3.10 ml (22.10 mmol) triethylamine in 150 ml ethanol was heated at reflux for 3 h. The resulting yellow suspension was filtered and the filtrate evaporated to dryness. The residue was suspended in ethyl acetate, filtered and the filtrate extracted with water. The organic layer was evaporated to dryness and the isolated crude product purified by silica gel chromatography (CH$_2$Cl$_2$/ethyl acetate 98:2) to yield 2.68 g (73%) of the title compound as a colorless oil. MS: 169.1 (M$^+$). $^1$H-NMR (300 MHz, CDCl$_3$): 2.74 (s, 1H); 5.47 (dd, J=11.1, 1.6 Hz, 1H); 5.97 (dd, 17.9, 1.6 Hz, 1H); 7.24 (d, J=8.4 Hz, 1H); 7.43 (t, J=7.7 Hz, 1H); 7.66 (dd, J=8.1, 1.2 Hz, 1H); 7.87 (dd, J=7.3, 1.2 Hz, 1H); 7.97 (d, J=8.4 Hz, 1H); 8.05 (dd, J=17.9, 11.1 Hz, 1H).

Example 9

[RuCl$_2$(ImH$_2$Mes)((2-methyl-8-quinolinyl)methylene)]

A suspension of 218 mg (0.26 mmol) of [RuCl$_2$(PCy$_3$)(ImH$_2$Mes)(phenylmethy-lene)], 26 mg (0.26 mmol) copper chloride and 49 mg (0.29 mmol) 2-methyl-8-vinyl-quinoline in 17 ml methylene chloride was stirred at 30° C. for 90 min. The reaction mixture was evaporated to dryness and the isolated crude product purified by silica gel chromatography (hexane/ethyl acetat 7:3) and finally digested in 15 ml hexane at room temperature for 30 min to yield 157 mg (96%) of the title compound as green crystals. MS: 632.9 ($M^+$). $^1$H-NMR (300 MHz, $C_6D_6$): 2.15 (s, 3H); 2.29 (s, 6H); 2.64 (s, 12H); 3.49 (s, 4H); 6.30 (d, J=8.4 Hz, 1H); 6.80 (t, J=7.3 Hz, 1H); 6.98 (s, 4H); 7.10 (d, J=8.4 Hz, 1H); 7.40 (d, J=8.1 Hz, 1H); 7.52 (d, J=7.0 Hz, 1H), 17.15-17.32 (br, 1H). Anal. calcd. for $C_{32}H_{35}N_3Cl_2Ru$: C, 60.66; H, 5.57; N, 6.63; Cl, 11.19. Found: C, 60.33; H, 5.58; N, 6.27; Cl, 10.90.

Example 10

[$RuCl_2$(tricyclohexylphosphine)((4-chloro-2-trifluoromethyl-8-quinolinyl)methylene)]

A suspension of 3.07 g (3.73 mmol) of [$RuCl_2(PCy_3)_2$ (phenylmethylene)] (commercial available from Sigma-Aldrich Inc., St. Louis, USA), 380 mg (3.84 mmol) copper chloride and 1.06 g (4.10 mmol) 4-chloro-2-trifluoromethyl-8-vinyl-quinoline in 135 ml methylene chloride was stirred at 30° C. for 90 min. The reaction mixture was evaporated to dryness and the isolated crude product purified by silica gel chromatography (hexane/ethyl acetat 2:1) and finally digested in 50 ml pentane at room temperature for 30 min to yield 429 mg (17%) of the title compound as dark green crystals. MS: 697.0 ($M^+$). $^{31}$P-NMR (121 MHz, $C_6D_6$): 54.2 ppm. $^1$H-NMR (300 MHz, $C_6D_6$): 1.18-2.35 (m, 30H); 2.60 (q, J=12.0 Hz, 3H); 6.82 (t, J=6.0 Hz, 1H); 7.01 (d, J=3.0 Hz, 1H); 7.55 (d, J=6.0 Hz, 1H); 7.89 (d, J=6.0 Hz, 1H); 17.80-17.90 (m, 1H).

Example 11

[$RuCl_2$(ImMes)((4-chloro-2-trifluoromethyl-8-quinolinyl)methylene)]

A suspension of 1.30 g (1.54 mmol) of [$RuCl_2(PCy_3)$(ImMes)(phenylmethylene)] (prepared according to J. Huang, E. Stevens, S. Nolan, J. Petersen, *J. Am. Chem. Soc.* 1999, 121, 2674-2678), 0.15 g (1.54 mmol) copper chloride and 435 mg (1.68 mmol) 4-chloro-2-trifluoromethyl-8-vinyl-quinoline in 100 ml methylene chloride was stirred at 30° C. for 90 min. The reaction mixture was evaporated to dryness and the isolated crude product purified by silica gel chromatography (hexane/ethyl acetate 5:2) to yield 260 mg (24%) of the title compound as orange crystals. MS: 719.0 ($M^+$). $^1$H-NMR (300 MHz, $C_6D_6$): 2.33 (s, 6H); 2.46 (s, 12H); 6.30 (s, 2H); 6.76 (dd, J=9.0, 6.0 Hz, 1H); 6.83 (s, 1H); 6.97 (s, 4H); 7.58 (d, J=6.0 Hz, 1H); 7.85 (d, J=9.0 Hz, 1H); 17.31-17.36 (m, 1H).

Application of Catalysts in Ring Closing Metathesis

Examples 12-18

Example 12

1-(Toluene-4-sulfonyl)-2,5-dihydro-1H-pyrrole

A solution of 257 mg (1.02 mmol) N,N-diallyl 4-methylbenzenesulfonamide (prepared according to S. Varray, R. Lazaro., J. Matinez, F. Lamaty, *Organometallics* 2003, 22, 2426-2435) and 19 mg (0.03 mmol) [$RuCl_2(ImH_2Mes)$((4-chloro-2-trifluoromethyl-8-quinolinyl)methylene)] in 5 ml toluene was stirred at 110° C. To monitor the conversion and selectivity, 0.2-ml samples were taken were after 1 h and 4 h. Each sample was filtered over a silica gel pad, the filtrate was evaporated to dryness and analyzed by GC (column: DB-1701; injector: 260° C.; detector: 260°; oven: 70 to 250° C./5° C. per min; carrier gas: $H_2$ (60 kPa); retention times: 15.5 min N,N-diallyl 4-methylbenzenesulfonamide, 24.5 min 1-(toluene-4-sulfonyl)-2,3-dihydro-1H-pyrrole, 25.5 min 1-(toluene-4-sulfonyl)-2,5-dihydro-1H-pyrrole). After 1 h (98% conversion), 96% of the title compound and 2% of 1-(toluene-4-sulfonyl)-2,3-dihydro-1H-pyrrole and after 4 h (100% conversion) 92% of the title compound and 8% of 1-(toluene-4-sulfonyl)-2,3-dihydro-1H-pyrrole were formed. $^1$H-NMR of 1-(toluene-4-sulfonyl)-2,5-dihydro-1H-pyrrole (300 MHz, $C_6D_6$): 2.43 (s, 3H); 4.12 (s, 4H); 5.65 (s, 2H); 7.32 (d, J=8.3 Hz, 2H); 7.73 (d, J=8.3 Hz, 2H). $^1$H-NMR of 1-(toluene-4-sulfonyl)-2,3-dihydro-1H-pyrrole (300 MHz, $C_6D_6$): 2.40-2.55 (m, 2H); 2.43 (s, 3H); 3.48 (t, J=8.9 Hz, 2H); 5.10-5.15 (m, 1H); 8.35-8.40 (m, 1H); 7.32 (d, J=8.3 Hz, 2H); 7.67 (d, J=8.3 Hz, 2H).

Example 13

For Comparison 1-(Toluene-4-sulfonyl)-2,5-dihydro-1H-pyrrole

In an analogous manner to Example 12 but in the presence of 17 mg (0.03 mmol) [$RuCl_2(ImH_2Mes)$((4-chloro-8-quinolinyl)methylene)] instead of [$RuCl_2(ImH_2Mes)$((4-chloro-2-trifluoromethyl-8-quinolinyl)methylene)] as catalyst, after 1 h (7% conversion), 7% of the title compound and after 4 h (15% conversion), 14% of the title compound and 1% of 1-(toluene-4-sulfonyl)-2,3-dihydro-1H-pyrrole were formed.

Example 14

For Comparison 1-(Toluene-4-sulfonyl)-2,5-dihydro-1H-pyrrole

In an analogous manner to Example 12 but in the presence of 16 mg (0.03 mmol) [$RuCl_2(ImH_2Mes)$ (8-quinolinylmethylene)] instead of [$RuCl_2(ImH_2Mes)$((4-chloro-2-trifluoromethyl-8-quinolinyl)methylene)] as catalyst, after 1 h (7% conversion), 7% of the title compound and after 4 h (31% conversion), 28% of the title compound and 3% of 1-(toluene-4-sulfonyl)-2,3-dihydro-1H-pyrrole were formed.

According to Barbasiewicz et al. (*Organometallics*, published on Web Jun. 17, 2006), a solution of 88 mg (0.35 mmol) N,N-diallyl 4-methylbenzenesulfonamide and 11.2 mg (0.018 mmol) [$RuCl_2(ImH_2Mes)$(8-quinolinylmethylene)] in 17.5 ml dichloromethane was stirred at room temperature. To monitor the conversion and selectivity, 0.2-ml samples were taken were after 4 h and 24 h. Each sample was filtered over a silica gel pad, the filtrate was evaporated to dryness and analyzed by GC as described in Example 12. After 4 h (2% conversion), 0.6% of the title compound and 0.3% of 1-(toluene-4-sulfonyl)-2,3-dihydro-1H-pyrrole and after 24 h (3% conversion) 1.5% of the title compound and 0.5% of 1-(toluene-4-sulfonyl)-2,3-dihydro-1H-pyrrole were formed.

Example 15

1-(Toluene-4-sulfonyl)-2,5-dihydro-1H-pyrrole

In an analogous manner to Example 12 but in the presence of 18 mg (0.03 mmol) [RuCl$_2$(ImH$_2$Mes)((4-hydroxy-2-phenyl-8-quinolinyl)methylene)] instead of [RuCl$_2$(ImH$_2$Mes)((4-chloro-2-trifluoromethyl-8-quinolinyl)methylene)] as catalyst, after 1 h (99% conversion) 98% of the title compound and 1% of 1-(toluene-4-sulfonyl)-2,3-dihydro-1H-pyrrole and after 4 h (100% conversion), 99% of the title compound and 1% of 1-(toluene-4-sulfonyl)-2,3-dihydro-1H-pyrrole were formed.

Example 16

1-(Toluene-4-sulfonyl)-2,5-dihydro-1H-pyrrole

In an analogous manner to Example 12 but in the presence of 18 mg (0.03 mmol) [RuCl$_2$(ImH$_2$Mes)((2-methyl-8-quinolinyl)methylene)] instead of [RuCl$_2$(ImH$_2$Mes)((4-chloro-2-trifluoromethyl-8-quinolinyl)methylene)] as catalyst, after 1 h (22% conversion) 11% of the title compound and after 4 h (66% conversion), 22% of the title compound and 5% of 1-(toluene-4-sulfonyl)-2,3-dihydro-1H-pyrrole were formed.

Example 17

1-(Toluene-4-sulfonyl)-2,5-dihydro-1H-pyrrole

In an analogous manner to Example 12 but in the presence of 16 mg (0.03 mmol) [RuCl$_2$(tricyclohexylphosphine)((4-chloro-2-trifluoromethyl-8-quinolinyl)methylene)] instead of [RuCl$_2$(ImH$_2$Mes)((4-chloro-2-trifluoromethyl-8-quinolinyl)methylene)] as catalyst, after 1 h (11% conversion) 7% of the title compound and 1% of 1-(toluene-4-sulfonyl)-2,3-dihydro-1H-pyrrole and after 4 h (42% conversion), 25% of the title compound and 1% of 1-(toluene-4-sulfonyl)-2,3-dihydro-1H-pyrrole were formed.

Example 18

1-(Toluene-4-sulfonyl)-2,5-dihydro-1H-pyrrole

In an analogous manner to Example 12 but in the presence of 20 mg (0.03 mmol) [RuCl$_2$(ImMes)((4-chloro-2-trifluoromethyl-8-quinolinyl)methylene)] instead of [RuCl$_2$(ImH$_2$Mes)((4-chloro-2-trifluoromethyl-8-quinolinyl)methylene)] as catalyst, after 1 h (53% conversion) 11% of the title compound and 11% of 1-(toluene-4-sulfonyl)-2,3-dihydro-1H-pyrrole, after 4 h (100% conversion), 54% of the title compound and 2% of 1-(toluene-4-sulfonyl)-2,3-dihydro-1H-pyrrole and after 20 h (100% conversion), 1% of the title compound and 64% of 1-(toluene-4-sulfonyl)-2,3-dihydro-1H-pyrrole were formed.

Application of Catalysts in Cross Metathesis

Examples 19-20

Example 19

(E)/(Z)-Diethyl 2-[3-cyano-2-propenyl]malonate

A solution of 100.0 mg (0.48 mmol) diethyl allylmalonate, 77.4 mg (1.45 mmol) acrylonitrile and 35.0 mg (0.05 mmol) [RuCl$_2$(ImH$_2$Mes)((4-chloro-2-trifluoromethyl-8-quinolinyl)methylene)] in 5 ml toluene was stirred at 110° C. To monitor the conversion and selectivity, 0.05-ml samples were taken were taken after 3 h and 40 h. Each sample was filtered over a silica gel pad, the filtrate was evaporated to dryness and analyzed by GC (column: HP-5, 5% phenyl methyl siloxan (Agilent 19091-413); injector: 250° C.; detector: 250° C.; oven: 100 to 150° C./5° C. per min, 5 min at 150° C., 150 to 200° C./5° C. per min and 200 to 300° C./20° C. per min; carrier gas: He (0.46 bar); retention times: 9.2 min diethyl allylmalonate, 17.5 min (Z)-diethyl 2-[3-cyano-2-propenyl]malonate and 18.8 min (E)-diethyl 2-[3-cyano-2-propenyl]malonate). After 3 h (66% conversion), 57% of the title compound and after 40 h (94% conversion) 83% of the title compound as an (E):(Z) mixture of 1:2 was formed. After evaporation of the solvent under reduced pressure, the crude product was purified by silica gel chromatography (cyclohexane/ethyl acetate 8:2) to yield 65.1 mg (60%) of the title compound as a (E):(Z) mixture of 1:2. MS: 226.3 (M$^+$). $^1$H-NMR of diethyl 2-[3-cyano-2-propenyl]malonate (300 MHz, C$_6$D$_6$): (Z)-isomer: 1.29 (t, J=7.1 Hz, 6H); 2.99 (td, J=7.1, 1.5 Hz, 2H); 3.51 (t, J=7.0 Hz, 1H); 4.20-4.24 (m, 4H); 5.40-5.42 (m, 1H); 6.54 (m, 1H). (E)-isomer: 1.28 (t, J=7.1 Hz, 6H); 2.79 (td, J=7.1, 1.5 Hz, 2H); 3.46 (t, J=7.1 Hz, 1H); 4.20-4.24 (m, 4H); 5.40-5.42 (m, 1H); 6.68 (m, 1H).

Example 20

(E)/(Z)-Diethyl 2-[3-cyano-2-propenyl]malonate

In an analogous manner to Example 19 but in the presence of 34.9 mg (0.05 mmol) [RuCl$_2$(ImMes)((4-chloro-2-trifluoromethyl-8-quinolinyl)methylene)] instead of [RuCl$_2$(ImH$_2$Mes)((4-chloro-2-trifluoromethyl-8-quinolinyl)methylene)] as catalyst, after 19 h (80% conversion), 48% of the title compound and after 40 h (87% conversion) 49% of the title compound as an (E):(Z) mixture of 1:2 was formed.

What is claimed:
1. A compound of the formula I

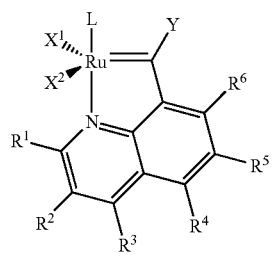

wherein L is a neutral ligand;
X$^1$ and X$^2$ independently of each other are anionic ligands;
R$^1$ is selected from the group consisting of C$_{1-6}$-alkyl, halogen-C$_{1-6}$-alkyl, C$_{1-6}$-alkoxy, C$_{1-6}$-alkylcarbonyl, aryl, hydroxy, aryloxy, nitro, amino, mono-C$_{1-6}$-alkyl- or di-C$_{1-6}$-alkylamino, halogen, thio, C$_{1-6}$-alkylthio or SO$_2$—C$_{1-6}$-alkyl, SO$_2$-aryl, SO$_3$H, SO$_3$—C$_{1-6}$-alkyl or OSi(C$_{1-6}$-alkyl)$_3$ and SO$_2$—NR'R" wherein R' and R" independently of each other have the meaning of hydrogen or C$_{1-6}$-alkyl or R' and R" together with the N atom form a carbocycle;
R$^2$, R$^3$, R$^4$, R$^5$ and R$^6$ independently of each other are selected from the group consisting of hydrogen, $C_{1-6}$-alkyl, halogen-$C_{1-6}$-alkyl, $C_{1-6}$-alkoxy, $C_{1-6}$-alkylcarbonyl, aryl, hydroxy, aryloxy, nitro, amino, mono-$C_{1-6}$-alkyl- or di-$C_{1-6}$-alkylamino, halogen, thio, $C_{1-6}$-alkylthio or $SO_2$—$C_{1-6}$-alkyl, $SO_2$-aryl, $SO_3H$, $SO_3$—$C_{1-6}$-alkyl or $OSi(C_{1-6}\text{-alkyl})_3$ and $SO_2$—NR'R" wherein R' and R" independently of each other have the meaning of hydrogen or $C_{1-6}$-alkyl or R' and R" together with the N atom form a carbocycle; and Y is selected from the group consisting of hydrogen, $C_{1-6}$-alkyl, $C_{2-6}$-alkenyl and aryl, or Y and $R^6$ taken together to form a (CH=CR)— or a —$(CH_2)_n$— bridge with n having the meaning of 2 or 3 and R is as defined for $R^2$.

2. The compound of claim 1 wherein

L is a neutral ligand selected from the group consisting of —$P(R^{10})_3$:

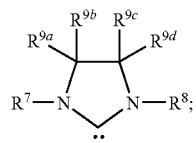

IIa

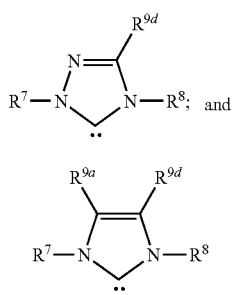

IIb

IIc wherein $R^7$ and $R^8$ independently of each other are $C_{1-6}$-alkyl, aryl, $C_{2-6}$-alkenyl or 1-adamantyl and $R^{9a\text{-}d}$ are independently of each other hydrogen, $C_{1-6}$-alkyl, $C_{2-6}$-alkenyl or aryl, or $R^{9b}$ and $R^{9c}$ or $R^{9a}$ and $R^{9d}$ taken together form a —$(CH_2)_4$-bridge;

$R^{10}$ is independently of each other $C_{1-6}$-alkyl, $C_{3-7}$-cycloalkyl, aryl or heteroaryl.

3. The compound of claim 2 wherein L is

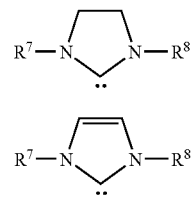

IId

IIe wherein $R^7$ and $R^8$ independently of each other are $C_{1-6}$-alkyl, aryl, $C_{2-6}$-alkenyl or 1-adamantyl.

4. The compound of claim 3 wherein $R^7$ and $R^8$ is 2,4,6-trimethylphenyl.

5. The compound of claim 4 wherein $X^1$ and $X^2$ independently of each other are a halogen.

6. The compound of claim 5 wherein $X^1$ and $X^2$ is chloro.

7. The compound of claim 6 wherein $R^1$ is $C_{1-6}$-alkyl, halogen $C_{1-6}$-alkyl or aryl.

8. The compound of claim 7 wherein $R^1$ is methyl, trifluoromethyl, ortho-tolyl, 2,6-dimethylphenyl or phenyl.

9. The compound of claim 8 wherein $R^3$ is hydrogen, hydroxy, $C_{1-6}$-alkoxy, nitro, amino or halogen.

10. The compound of claim 9 wherein $R^2$, $R^4$, $R^5$ and $R^6$ are hydrogen.

11. A process for the preparation of a compound of claim 1 which comprises the transformation of a Ru-precursor compound of the formula

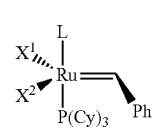

III wherein $X^1$ and $X^2$ independently of each other are anionic ligands, Cy is cyclohexyl and Ph is phenyl with a compound of formula IV

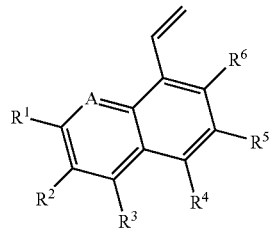

IV wherein $R^1$ is selected from the group consisting of $C_{1-6}$-alkyl, halogen-$C_{1-6}$-alkyl, $C_{1-6}$-alkoxy, $C_{1-6}$-alkylcarbonyl, aryl, hydroxy, aryloxy, nitro, amino, mono-$C_{1-6}$-alkyl- or di-$C_{1-6}$-alkylamino, halogen, thio, $C_{1-6}$-alkylthio or $SO_2$—$C_{1-6}$-alkyl, $SO_2$-aryl, $SO_3H$, $SO_3$—$C_{1-6}$-alkyl or $OSi(C_{1-6}\text{-alkyl})_3$ and $SO_2$—NR'R" wherein R' and R" independently of each other have the meaning of hydrogen or $C_{1-6}$-alkyl or R' and R" together with the N atom form a carbocycle; and $R^2$, $R^3$, $R^4$, $R^5$ and $R^6$ independently of each other are selected from the group consisting of hydrogen, $C_{1-6}$-alkyl, halogen-$C_{1-6}$-alkyl, $C_{1-6}$-alkoxy, $C_{1-6}$-alkylcarbonyl, aryl, hydroxy, aryloxy, nitro, amino, mono-$C_{1-6}$-alkyl- or di-$C_{1-6}$-alkylamino, halogen, thio, $C_{1-6}$-alkylthio or $SO_2$—$C_{1-6}$-alkyl, $SO_2$-aryl, $SO_3H$, $SO_3$—$C_{1-6}$-alkyl or $OSi(C_{1-6}\text{-alkyl})_3$ and $SO_2$—NR'R" wherein R' and R" independently of each other have the meaning of hydrogen or $C_{1-6}$-alkyl or R' and R" together with the N atom form a carbocycle.

12. A process for performing ring closing metathesis, said process comprising contacting a diterminal diene with a compound of formula I according to claim 1.

13. A process for performing cross metathesis, said process comprising contacting two alkenes with terminal vinyl function with a compound of formula I according to claim 1.

* * * * *